(12) United States Patent
Wang

(10) Patent No.: US 8,213,698 B2
(45) Date of Patent: Jul. 3, 2012

(54) SYSTEMS AND METHODS FOR CAPSULE CAMERA CONTROL

(75) Inventor: Kang-Huai Wang, Saratoga, CA (US)

(73) Assignee: Capso Vision Inc., Saratoga, CA (US)

( * ) Notice: Subject to any disclaimer, the term of this patent is extended or adjusted under 35 U.S.C. 154(b) by 277 days.

(21) Appl. No.: 12/776,428

(22) Filed: May 10, 2010

(65) Prior Publication Data

US 2010/0220179 A1 Sep. 2, 2010

Related U.S. Application Data

(63) Continuation-in-part of application No. 11/533,304, filed on Sep. 19, 2006, now Pat. No. 7,983,458.

(51) Int. Cl.
*G06K 9/00* (2006.01)

(52) U.S. Cl. .................. 382/128; 382/272; 600/101

(58) Field of Classification Search .................. 382/128
See application file for complete search history.

(56) References Cited

U.S. PATENT DOCUMENTS

| 6,939,292 | B2 * | 9/2005 | Mizuno | 600/118 |
| 7,343,036 | B2 * | 3/2008 | Kleen et al. | 382/154 |
| 7,953,261 | B2 * | 5/2011 | Nishimura et al. | 382/128 |
| 8,116,531 | B2 * | 2/2012 | Kanda | 382/107 |
| 2006/0120484 | A1 * | 6/2006 | Matsumoto et al. | 375/316 |
| 2007/0098379 | A1 | 5/2007 | Wang et al. | |
| 2007/0165932 | A1 * | 7/2007 | Nishimura et al. | 382/128 |
| 2007/0191677 | A1 * | 8/2007 | Nishimura et al. | 600/109 |
| 2007/0221233 | A1 * | 9/2007 | Kawano et al. | 128/899 |
| 2007/0232851 | A1 * | 10/2007 | Fujimori et al. | 600/109 |
| 2007/0242132 | A1 * | 10/2007 | Homan et al. | 348/65 |
| 2008/0143822 | A1 | 6/2008 | Wang et al. | |
| 2009/0148014 | A1 * | 6/2009 | Kanda | 382/128 |
| 2009/0225158 | A1 * | 9/2009 | Kimoto | 348/77 |
| 2009/0292174 | A1 * | 11/2009 | Shigemori | 600/117 |
| 2011/0069876 | A1 * | 3/2011 | Kanda | 382/134 |
| 2011/0085717 | A1 * | 4/2011 | Matsuda | 382/128 |
| 2012/0051612 | A1 * | 3/2012 | Kitamura et al. | 382/128 |

* cited by examiner

*Primary Examiner* — Sath V Perungavoor
(74) *Attorney, Agent, or Firm* — Blairtech Solution LLC

(57) ABSTRACT

Systems and methods are provided for environment change sensing corresponding to the capsule camera entering the colon from the small intestine. In the environment change sensing mode, the capsule camera is operated in a very low power mode by configuring the image sensor to use a small region of interest or a high sub-sampling ratio. Image data is processed to estimate the light level. The variation of light level is used to detect environment change corresponding to entering the colon from the small intestine. Alternatively, the motion metric for a current frame and a reference frame is evaluated. The characteristic of the motion metric is extracted and used to detect environment change. In another configuration, the system determines environment change based on a combination of the variation of light intensity and the characteristic of the motion metric. Upon the detection of capsule camera entrance into the colon from the small intestine, control signals are provided to the image sensor and the light source.

19 Claims, 11 Drawing Sheets

SYSTEMS AND METHODS FOR CAPSULE CAMERA CONTROL

CROSS REFERENCE TO RELATED APPLICATIONS

The present invention is related and claims priority to US patent application, entitled "In Vivo Autonomous Camera with On-Board Data Storage or Digital Wireless Transmission in Regulatory Approved Band", Ser. No. 11/533,304, filed on Sep. 19, 2006. The U.S. Non-Provisional patent application is hereby incorporated by reference in its entirety.

FIELD OF THE INVENTION

The present invention relates to diagnostic imaging inside the human body. In particular, the present invention relates to detecting the entrance of the capsule camera into the colon from the small intestine and controlling capsule camera accordingly, wherein the capsule camera has on-board storage or wireless transmission.

BACKGROUND

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia. Endoscopies are necessarily inpatient services that involve a significant amount of time from clinicians and thus are costly.

An alternative in vivo image sensor that addresses many of these problems is capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. patent application Ser. No. 11/533,304, entitled "In Vivo Autonomous Camera with On-Board Data Storage or Digital Wireless Transmission in Regulatory Approved Band," filed on Sep. 19, 2006. This application describes a motion detection is conducted using a portion of each image, the portion being stored in a partial frame buffer. In one embodiment, two partial frame buffers are used as an operand buffers for a reduced version of a current image and a reference image, respectively. The reference frame buffer corresponds to the one containing a previously stored or transmitted digital image. When the image in the operand partial frame buffer is determined not to be stored, that partial frame buffer may be overwritten by the next digital image to be motion-detected. Otherwise, the operand partial frame buffer would be designated the next reference partial frame buffer, and the current reference partial frame buffer is designated the next operand partial frame buffers. In the above application, a metric for measuring the degree of motion between the two partial images described and is used to compare with a threshold as to whether to capture an underlying image or as to determine a proper compression ratio for the underlying image.

While the motion detection has greatly helped to eliminate some unnecessary image capture and conserved the precious on-board storage and battery power, it may not fully address dynamic environmental issue. The environment in the small intestine and that in the colon may present very different imaging environment. For example, the small intestine has a smaller average diameter than the colon. Therefore, the distance between the capsule camera and a non-contacting lumen wall being imaged is closer for the small intestine than the colon. Furthermore, the average transit time for the capsule camera to travel through the small bowel is about 5 hours while the average transit time to travel through the colon is about 30 hours. On the other hand, the length of the former is about 6 meters and the latter is about 1.5 meters. Therefore, the average transit speed in the small intestine is about 20-30 times faster than the transit speed in the colon. The average transit speed can also be used as an indication to differentiate the environment between the small intestine and the colon.

Furthermore, a combination of the distance between the camera and lumen walls and the average transit speed are useful information to differentiate the environment between inside the intestine and inside the colon. For a capsule camera intended to image the colon, it will be beneficial that the capsule camera is able to detect the environment change when the capsule camera enters the colon from the small intestine. Accordingly, the capsule camera may be operated in a very low power mode and/or a mode where the archive memory is not filled up as quickly as normal mode before it enters the colon. Therefore, it is desirable to develop systems and methods that provide environment change detection and configure the capsule camera accordingly depending on the environment. For a capsule camera intended for imaging the colon, the system may provide control signals required to configure the capsule camera to capture and store images with adequate quality and illuminating light when the detection of the environment change corresponding to entrance into the colon from the small intestine is asserted.

BRIEF SUMMARY OF THE INVENTION

The present invention provides methods and systems with environment change sensing mode and controls the capsule camera having on-board image storage or wireless transmitter accordingly depending on the environment detected. The environment sensing regarding whether the capsule camera is in the small intestine or the colon is determined according to the variation of received light level. In one embodiment of the present invention, the variation of light level is calculated using the light level weighted by the luminous energy of at least one light source, i.e., a product of the exposure time and the output light intensity of the at least one light source. An environment change corresponding to an entrance into the colon from the small intestine is detected according to the variation of received light level. According to one embodiment of the present invention, the system provides an image sensor control to the image sensor and/or provides a light source control to the at least one light source so that the capsule camera will operate in an intended mode to capture and store images in a desired quality upon the detection of entrance into the colon from the small intestine.

According to another embodiment of the present invention, the system uses a light sensing device to detect the scattered light bounced from lumen walls. In yet another embodiment of the present invention, the variation of light level is calculated using the light level weighted by the luminous energy of at least one light source, i.e., a product of the exposure time and the output light intensity of the at least one light source. In one embodiment of the present invention, the variation is determined based on a current light level and a plurality of past light levels. In yet another embodiment of the present invention, the variation is determined according to the moving average of a current light level and a plurality of past light levels. In an alternative embodiment of the present invention, the variation of light levels is determined according to the difference between the moving average and an initial average light level. In yet another embodiment of the present invention, the variation is determined according to the ratio of the moving average to an initial average light level.

According to another embodiment of the present invention, the motion metric between a current frame and a previous frame is measured. The environment of the capsule camera is detected based on characteristic of the motion metric. In one embodiment, the motion metric is compared with a threshold to determine whether motion between the current frame and the reference frame exceeds the threshold. The average camera transit speed is then estimated based on the motion decision for the image frame over a period of time. The characteristic of the motion metric is then determined based on a change in the average camera transit speed. If the change is above a given threshold, it may indicate an environment change corresponding to the entrance of the capsule camera into the colon from the small intestine. According to one embodiment of the present invention, the system provides an image sensor control to the image sensor and/or provides a light source control to the at least one light source so that the capsule camera will operate in an intended mode to capture and store images in a desired quality and image pixel level upon the detection of entrance into the colon from the small intestine.

Upon the detection of environment change corresponding to the entrance of the capsule camera into the colon from the small intestine, the system may provide control for the capsule camera operations such as the sub-sampling rate, the region of interest (ROI) of the image sensor, frame rate or captured frame rate, according to one embodiment of the present invention. Furthermore, upon the detection of environment change, the system may also provide light source control to adjust the output light intensity and/or the exposure time of the at least one light source. In one embodiment of the current system and method, at least one light sensor is used as the light detecting device. Alternatively, the image sensor of the capsule camera is used as the light detecting device.

In yet another embodiment of the present invention, both the received light scattered from lumen walls and the characteristic of the motion metric measured between a current frame and a reference frame are used to detect environment change corresponding to the entrance of the capsule camera into the colon from the small intestine. The variation of the light level is derived from the received light scattered from lumen walls. On the other hand, the characteristic of the motion metric is based on the variation of the average camera transit speed. Both the variation of the light level and the characteristic of the motion metric are combined and used to determine the environment change corresponding to the entrance of the capsule camera into the colon from the small intestine.

DETAILED DESCRIPTION OF THE INVENTION

Autonomous encapsulated cameras offer a much more comfortable means for imaging body cavities or passages in vivo than the conventional endoscopes. Through the course of imaging the body cavities, a large volume of images in the order of tens of thousands are expected to be acquired. While technology advancement has helped to reduce the power consumption for illuminating the lumen walls and imaging the organs, as well as to improve the battery capacity, nevertheless, it is still an issue to have the capsule camera reliably image the colon and to further conserve the power. The passage rate for a swallowable camera is about 4 to 8 hours in the small intestines and it may take 12 hours or longer for the capsule camera to go through the colon even with the aid of motility enhancer. While the typical passage rate for swallowable camera in the small intestine is about 4 to hours, there are substantial variation in passage rate in the small intestine from person to person. In order to ensure that an autonomous capsule camera will start to image the colon reliably, the capsule camera is often configured to enter monitor and capture mode shortly after the capsule camera is administered. The starting time may be as short as 1 hour after swallow in order to achieve high reliability for the capsule camera to start imaging in the colon. The need for high reliability for early camera start results in waste of power when the capsule camera unnecessarily starts to monitor and capture images before the capsule camera enters the colon.

A system and method embodying the present technique detects the scattered light bounced from the lumen wall and determines whether there is an environment change that indicates the entrance into the colon from the small intestine. Before the capsule camera enters the colon, it remains in a very low power mode or a mode with low consumption of archiving capacity while determining whether there is an environment change. If the environment change is detected, the system may provide a control signal to turn the capsule camera into a normal operation mode to monitor, capture and store images.

Figure 1A:
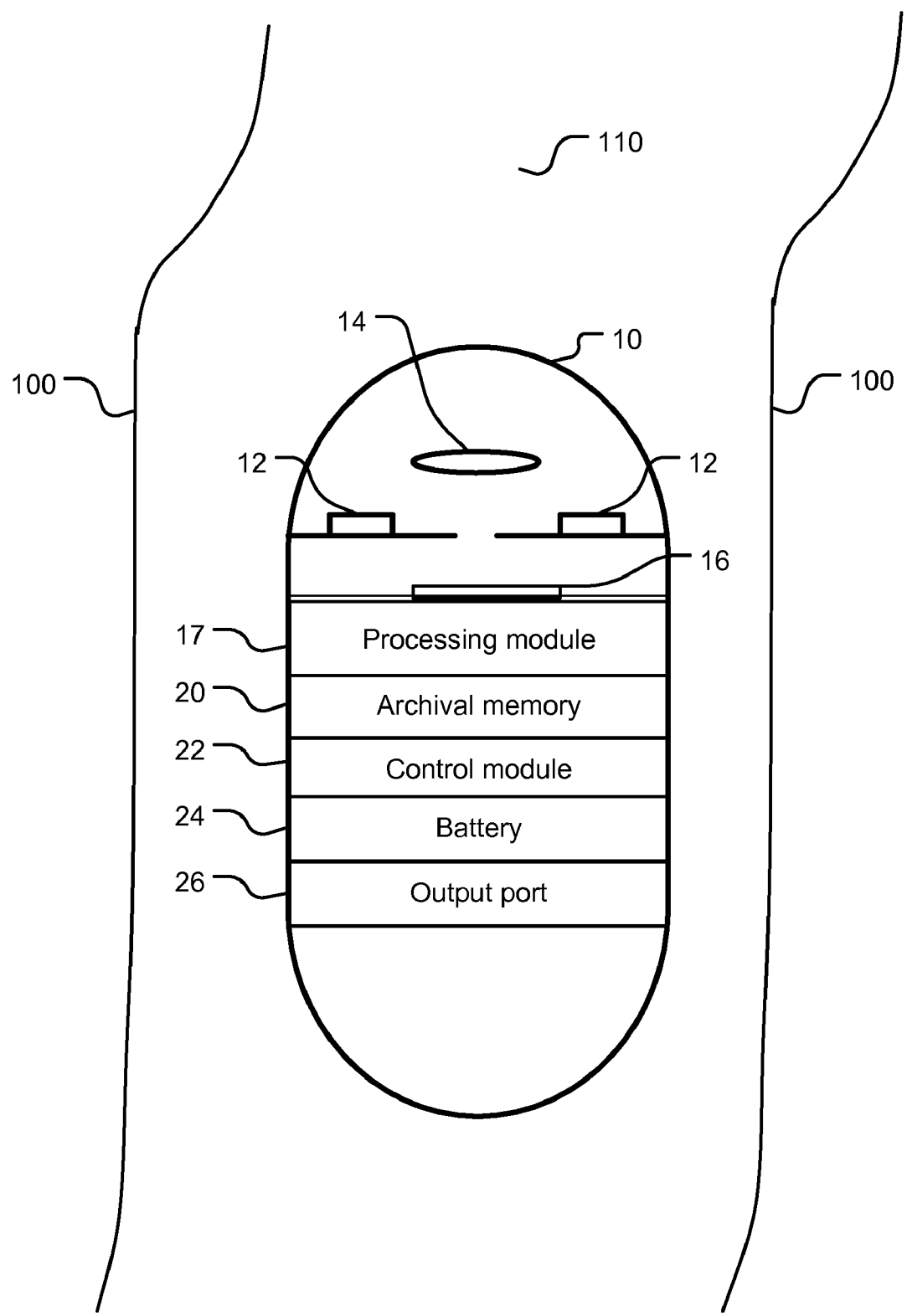
FIG. 1A shows schematically a capsule camera system having on-board storage, according to one embodiment of the present invention, where the capsule camera shown is inside the GI tract.

FIG. 1A shows a swallowable capsule system 110 inside body lumen 100, in accordance with one embodiment of the present invention. Lumen 100 may be, for example, the colon, small intestines, the esophagus, or the stomach. Capsule system 110 is entirely autonomous while inside the body, with all of its elements encapsulated in a capsule housing 10 that provides a moisture barrier, protecting the internal components from bodily fluids. Capsule housing 10 is transparent or partially transparent, so as to allow light from the light-emitting diodes (LEDs) of illuminating system 12 to pass through the wall of capsule housing 10 to the lumen 100 walls, and to allow the scattered light from the lumen 100 walls to be collected and imaged within the capsule. Capsule housing 10 also protects lumen 100 from direct contact with the foreign material inside capsule housing 10. Capsule housing 10 is provided a shape that enables it to be swallowed easily and later to pass through of the GI tract. Generally, capsule housing 10 is sterile, made of non-toxic material, and is sufficiently smooth to minimize the chance of lodging within the lumen.

As shown in FIG. 1A, capsule system 110 includes illuminating system 12 and a camera that includes optical system 14 and image sensor 16. An image captured by image sensor 16 may be processed by a processing module 17, which determines whether there is an environment change corresponding to the entrance from small intestine to the colon. Processing module 17 may be implemented in software that runs on a digital signal processor (DSP) or a central processing unit (CPU), in dedicated hardware, or a combination of both software and hardware. A semiconductor nonvolatile archival memory 20 may be provided to allow the images to be retrieved at a docking station outside the body, after the capsule is recovered. System 110 includes battery power supply 24 and an output port 26. Capsule system 110 may be propelled through the GI tract by peristalsis.

Illuminating system 12 may be implemented by LEDs. In FIG. 1A, the LEDs are located adjacent the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. The control module 22 usually is responsible for overall system operation and may contain a microcontroller or a digital signal processing. In practice, the processing module 17 and the control module 22 may be integrated into a single unit. However, for the purpose of describing the processing required to implement the technique of determining environment change corresponding to entrance of the colon from small intestine, a separate processing module is illustrated. As to be described later, processing module 17 may also be responsible for certain control functions associated with the present technique such as providing image sensor control to the image sensor and light source control to at least one light source illuminating the lumen wall. The images are stored in an on-board archival memory system 20. The output port 26 shown in FIG. 1A is not operational in vivo but uploads data to a work station after the capsule is recovered, having passed from the body.

Figure 1B:
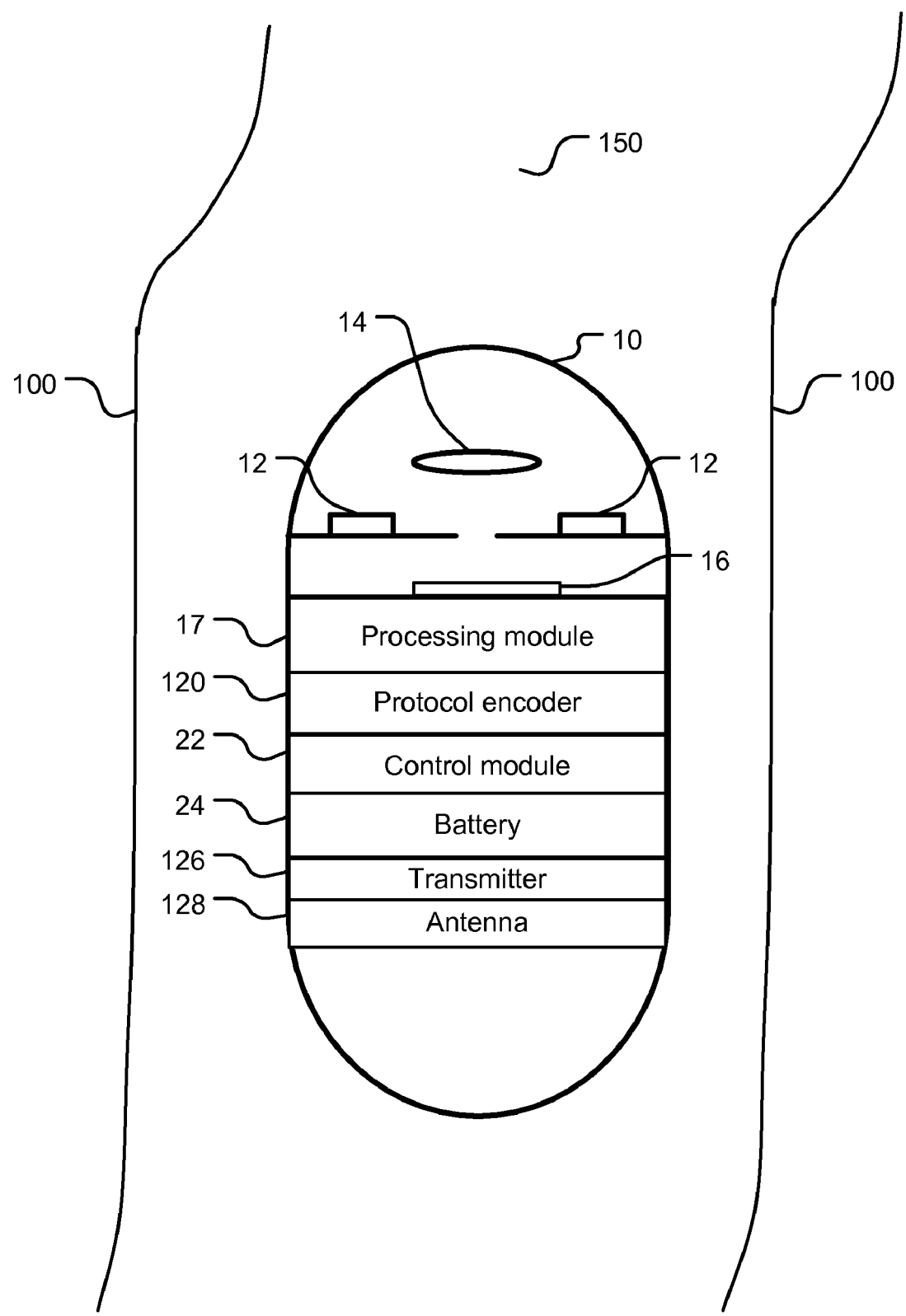
FIG. 1B shows schematically a capsule camera system having a wireless transmitter, according to one embodiment of the present invention, where the capsule camera shown is inside the GI tract.

The present invention is also used for capsule camera system having a wireless transmitter to send the captured images to an external receiver instead of storing the images on board. FIG. 1B shows swallowable capsule system 150, in accordance with one embodiment of the present invention. Capsule system 150 may be constructed substantially the same as capsule system 110 of FIG. 1, except that archival memory system 20 and output port 26 are no longer required. Capsule system 150 also includes communication protocol encoder 120, transmitter 126 and antenna 128 that are used in the wireless transmission. The elements of capsule 110 and capsule 150 that are substantially the same are therefore provided the same reference numerals. Their constructions and functions are therefore not described here again. Communication protocol encoder 120 may be implemented in software that runs on a DSP or a CPU, in hardware, or a combination of software and hardware. Transmitter 126 and antenna system 128 are used for transmitting the captured digital image.

In the present invention, the capsule camera system is operated in a very low power mode until the capsule camera reaches the section of body cavities that it intends to image. For example, the capsule camera system may be designed to capture images in the colon. Therefore, the capsule camera may be placed in an "environment change sensing" mode after it is swallowed. In the environment change sensing mode, the capsule camera system monitors the surrounding environment to detect any significant changes, particularly the changes in scattered light bounced back from the lumen wall. A noticeable change in scattered light may indicate environment change corresponding to capsule camera entrance into the colon from the small intestine.

In a capsule camera system, a light source such as the LED is used to illuminate lumen walls. The image sensor senses the image by collecting light reflected from the respective lumen walls being imaged. The signal sensed by sensor cells is a voltage signal which is converted into a digital signal using an analog to digital converter (ADC). The voltage signal from the sensor cell is usually proportional to the light energy, also called luminous energy collected by the sensor cells when the sensor is operated in a linear mode having the input light energy within its dynamic range. The light energy or the luminous energy is calculated from the light power integrated over a period of time that the sensor is collecting light, where the light power is proportional to the light intensity. Inside the lumen, the environment is dark unless the LED is turned on to illuminate lumen walls. The light energy can be estimated from the product of light power and the LED exposure time, i.e., the period of time that the LED is turned on. For a point light source, the light power or light intensity can be approximated by the inverse square law of the distance between the light source and a location being measured. However, the inverse square law may not be an accurate model for the capsule camera configuration due to the short distance between the LED and lumen walls. Nevertheless, the light intensity, L, reflected from lumen walls can be modeled as $L \propto 1/d^x$, where $0 < x \leq 2$, where d is the distance between the LED and the lumen wall being imaged. While the above mathematical model for light intensity versus distance is helpful to appreciate the relationship between the light intensity and the distance, the above mathematical model is not limitation of the present invention. As it will become clear in this disclosure that the present invention relies on the fact that the light intensity versus the distance is a monotonic function. Therefore, a larger distance will always result in a lower light intensity when all other conditions remain the same and the light level will provide useful information about the distance between the capsule camera and the lumen wall.

Figure 2A:
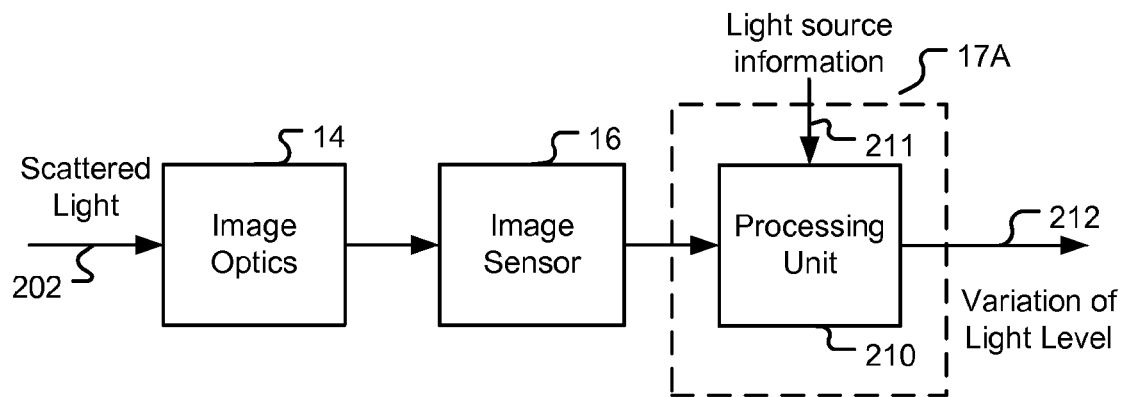
FIG. 2A shows a functional block diagram according to one exemplary embodiment of the present system to determine environment change.

FIG. 2A illustrates an example of a capsule camera having a processing module 17A to practice one embodiment of the present technique, where only the components involved with the underlying processing are shown. The image optics, i.e., lens 14 allows scattered light 202 bounced from the lumen walls 100 to be collected and imaged by the image sensor 16. The image data from image sensor 16 is then processed by the processing module 17A which comprises a processing unit 210. The processing module 17A processes the image data to determine the light level based on the image data. The pixel value of the image data is substantially proportional to the luminous energy when the image sensor is operated in the linear range. Therefore, the image data provides a measurement of the luminous energy received at the image sensor. In other words, the light level derived from the image data is a measurement of the luminous energy. The LEDs used in the system may provide fixed light intensity and a fixed exposure time in operation mode. For example, if the capsule camera in tended to image the colon port of the intestine, the camera can be operated in a very low power mode to evaluate whether the environment change corresponding to entering the colon occurs. The very low power mode usually is started a few hours after the capsule camera is swallowed to take into account of the time for the camera to enter the small intestine. In this very low power mode, the LEDs only require to provide sufficient luminous energy for the image sensor to provide sufficient image quality for assessment of environment change. However, if the luminous energy from LEDS varies under light source control, the variation of the luminous energy has to be taken into account in the light level evaluation. In this case, the light level is weighted by the luminous energy of the light source such as the LED in the illuminating system 12 in FIGS. 1A and 1B. The light source information 211 is usually available from the light source control parameters, such as the exposure time, and the current for the LED that directly affects the light intensity. While the light source information 211 is shown as an input from other part of the capsule camera to the processing unit 210, the light source information may be readily available from the processing unit 210, as shown in FIGS. 2C and 2D. Since the processing unit 210 provides needed information to the light control unit 230, the processing unit 210 may be able to determine the light control parameters to be applied in the next instance. In the case that the light source provides variable luminous energy, the processing module 17A furthermore determines variation of weighted light level 212 along time.

Figure 2B:
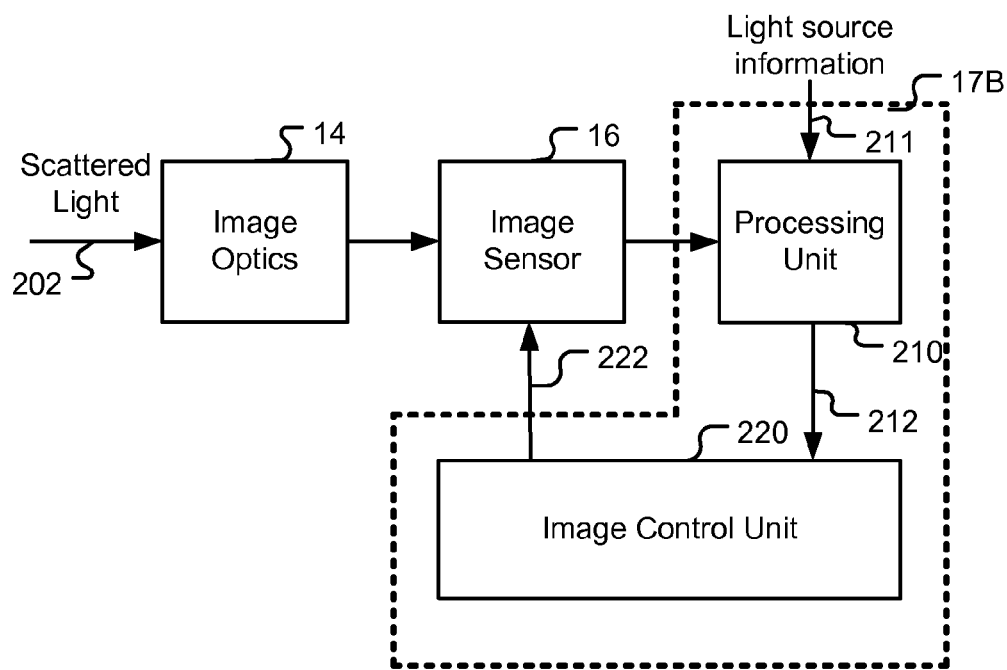
FIG. 2B shows a functional block diagram according to another exemplary embodiment of the present system to determine environment change.
Figure 2C:
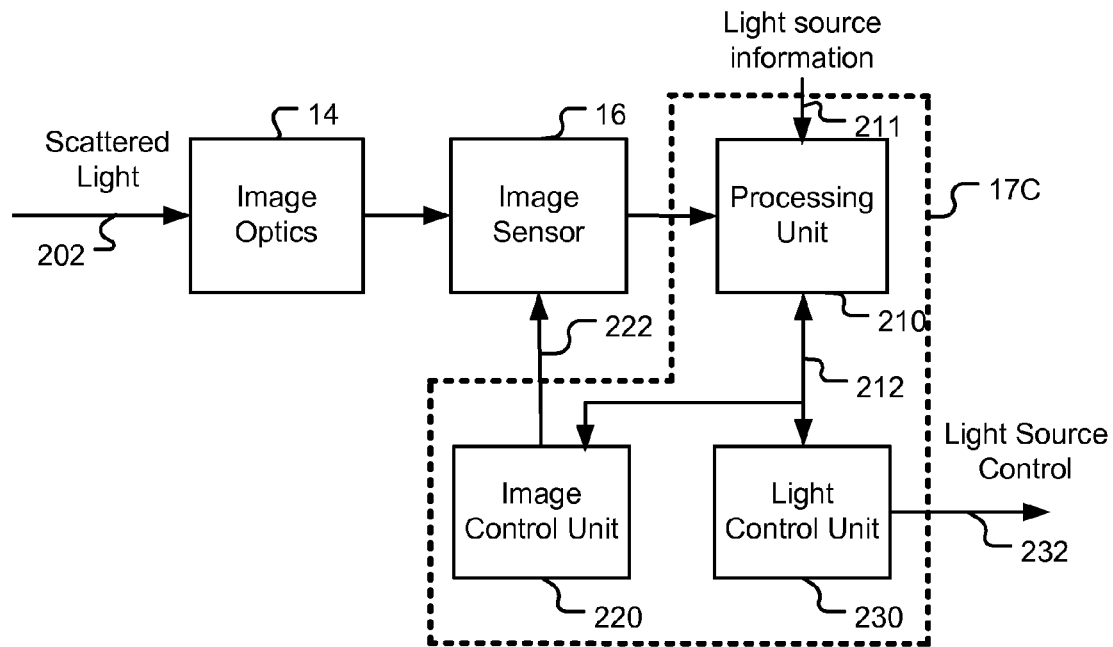
FIG. 2C shows a functional block diagram according to yet another exemplary embodiment of the present system to determine environment change.
Figure 2D:
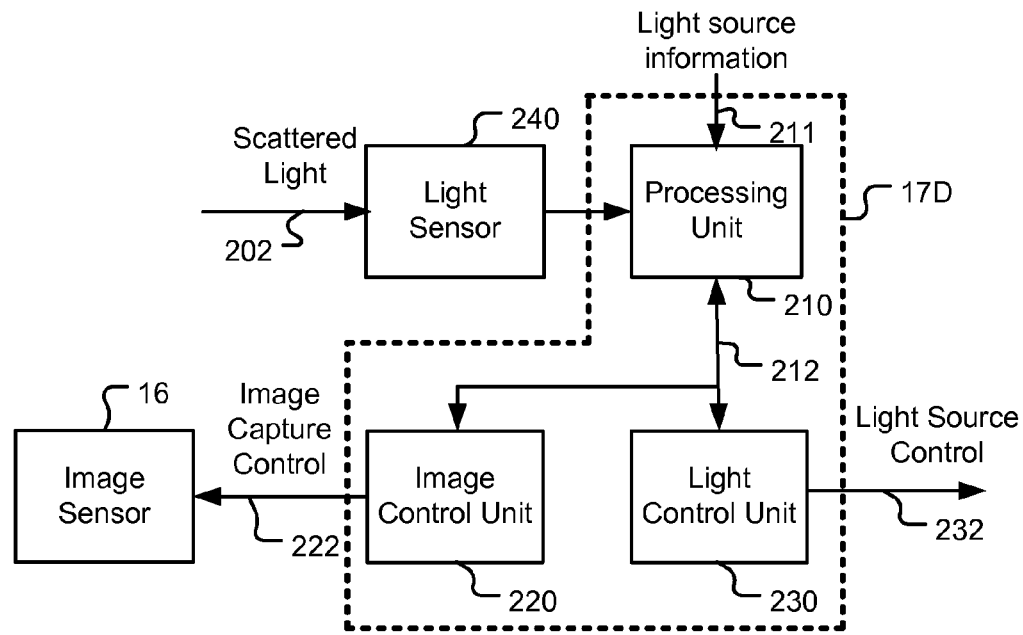
FIG. 2D shows a functional block diagram according to one exemplary embodiment of the present system to determine environment change where a light sensor is used as the light detecting device.

FIG. 2B illustrates an example of a capsule camera having a processing module 17B to practice another embodiment of the present technique. Compared with the system in FIG. 2A, the system in FIG. 2B further comprises an image control unit 220, which receives variation of light level 212 from the processing unit 210. The image control unit 220 of the processing module 17B provides image control signal 222 to the image sensor 16 based on the variation of light level 212. The image control signal adjusts the setting of the image sensor 16 appropriate for the capsule camera environment. For example, if the capsule camera is intended for imaging the colon, the capsule camera does not need to actively monitor and capture images in the small intestine. Accordingly, the image sensor 16 can be configured to a mode that is sufficient to determine light level from the image data without the cost of higher power consumption for operating the image sensor 16 at normal spatial resolution and/or frame rate. For example, a very small region of interest (ROI), such as ($\frac{1}{16}$) of the original horizontal size and ($\frac{1}{16}$) of the original vertical size, can be used for detecting light level of the image data. Lowering the frame rate is another effective way to lower power consumption of the image sensor 16. The image sensor 16 consumes much less power with a ROI of ($\frac{1}{16}$)×($\frac{1}{16}$) of the original size. Nevertheless, such small ROI is adequate for the purpose of determining the light level of image data sensed by the image sensor 16. While a ROI of ($\frac{1}{16}$)×($\frac{1}{16}$) is used as an example, other ROI sizes may also be used to achieve the goal of determining light level while conserving the image sensor power. Alternatively, a sub-sampling mode may be used for the image sensor 16 to determine light level with reduced power consumption. For example, the sampling rate can be adjusted to ($\frac{1}{16}$) of the normal sampling rate horizontally and vertically which will result in the same image size as the case with a ROI of ($\frac{1}{16}$)×($\frac{1}{16}$) of the original size. Lowering the frame rate is another means to reduce image sensor power which can be used separately or in combination with the ROI or sub-sampling technique to conserve image sensor power. While using image sensor control to cause the image sensor to output image data at reduced size can help to reduce power consumption associated with image-based light intensity computation, not all image sensors support built-in size reduction feature. Nevertheless, the present invention can still be practiced by using full-sized image to compute the image intensity. On the other hand, the power consumption based on current microelectronic technology, such as ASIC (Application Specific Integrated Circuit), becomes much more power efficient than before. Therefore, the power consumption associated with intensity computation based on a full-size image will not deter the present invention.

FIG. 2C illustrates an example of a capsule camera having a processing module 17C to practice yet another embodiment of the present technique. Compared with the system in FIG. 2B, the system in FIG. 2C further comprises a light control unit 230, which receives variation of light level 212 from the processing unit 210. The light control unit 230 of the processing module 17C provides light control signal 232 to the light source, i.e., LED in the illuminating system 12 based on the variation of light level 212. The light control signal can be used to adjust the configuration of the illuminating system 12 appropriate for the capsule camera environment. In a capsule camera system, both the illuminating system 12 and image sensor 16 consume substantial power. Therefore, by lowering the power consumption of the image sensor 16 along may not be sufficient to conserve power in the environment change sensing mode, especially when the frame rate is at a normal rate and the LED illumination is at normal level. Since the purpose of the environment change sensing mode is to detect the environment change, the image data is mainly used for determining the light level and therefore the image quality of the image data is not a concern. Consequently, it is desirable to further conserve power in the environment change sensing mode by lowering the light output from the illuminating system 12. The LED light output can be set to a low level before the capsule camera is detected entering the colon.

While the systems in FIGS. 2A-2C illustrate examples of using the image sensor already existing in the capsule camera as the light sensing device for cost and space saving purposes, a dedicated light sensor 240 can be used as shown in FIG. 2D. Compared with the image sensor 16 in the cases of FIGS. 2A-2C, the use of a light sensor 240 consumes much less power than the image sensor 16. The choice between an existing image sensor 16 and an additional dedicated light sensor for the light sensing device is a matter of system design tradeoffs. From processing point of view, both systems have most processing identical except for some differences in pre-processing of intensity level from the image data of an image frame. The examples in FIGS. 2A-2D illustrates the image sensor and the light source are adjusted in response to the mode of operation based on the variations of light level, other system parameters or functions may also be adjusted in response to the mode of operation. For example, the mode of operation may also determine the decisions regarding whether to store the image in the case of capsule 110 compression having an on-board storage, whether to transmit the image data in the case of capsule 150 having a wireless transmitter, and whether to apply compression (optional and not shown in the Figures) to the image data to be stored or transmitted.

Figure 3A:
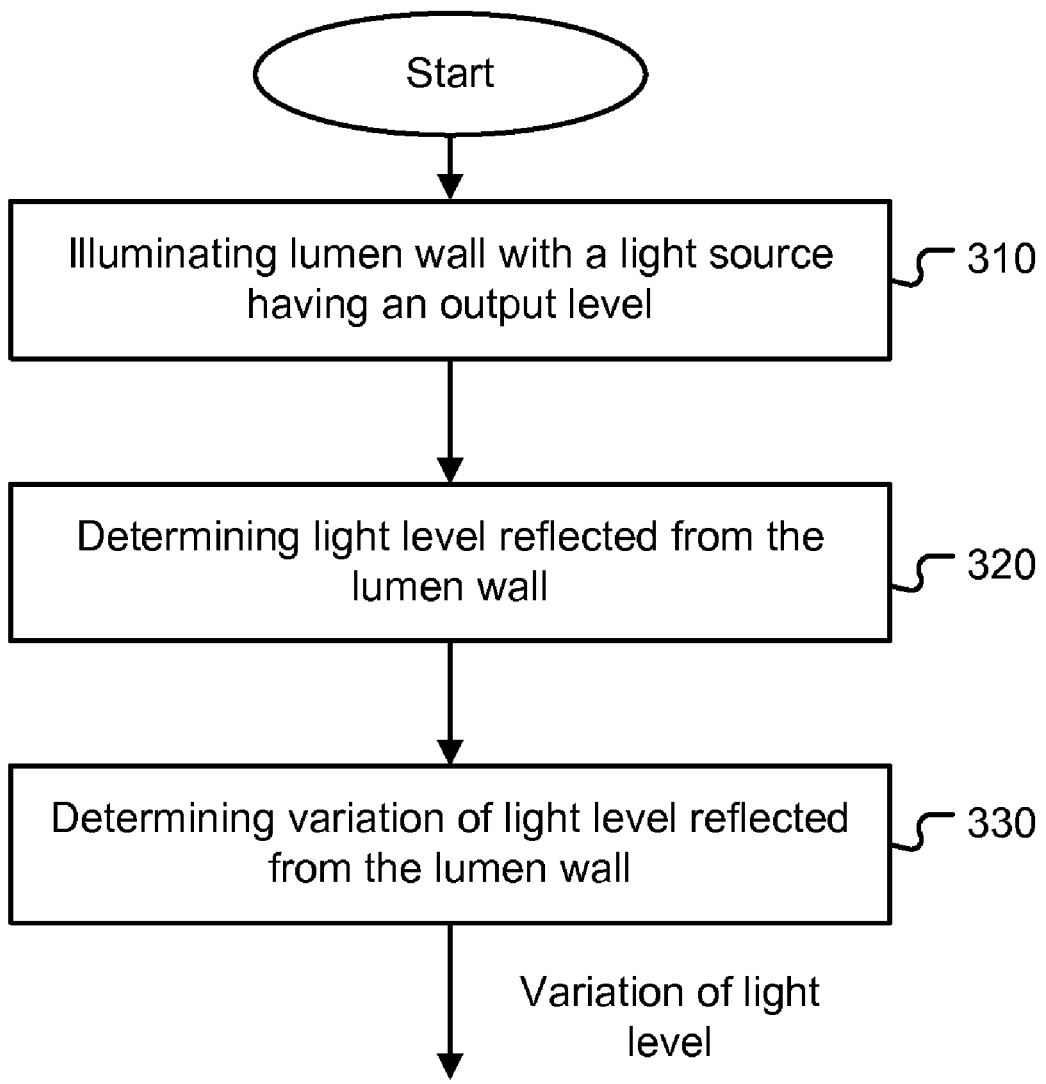
FIG. 3A is a flow chart illustrating exemplary processing to determine capsule camera environment change according to one embodiment of the present system.

FIG. 3A illustrates an exemplary flow chart corresponding to the system of FIG. 2A. The method according to the present invention illuminates lumen wall with a light source having an output light intensity and an exposure time in step 310. The LED output intensity is substantially linearly proportion to the current flowing through it. The LED driver circuit typically consists of a controller and a driver and often these two modules are integrated. The light source control usually is applied to adjust the LED control/driving parameters, such as the current flowing through the LED and the duration that the LED is turned on. The method then determines the light level reflected from the lumen walls 320. Furthermore, the method determines the variation of light level associated with the scattered light bounced from the lumen wall. The variation of light level is provided by the system as an output signal. If the light level Or in this environment sensing more the light could be a constant so the weighted result is just the value from the sensor since division is a difficult function to implement in hardware or software/firmware. As mentioned earlier, the luminous energy from the light source may be varied instead of fixed. In such case, the light level has to take into consideration of the variation of the luminous energy by using a weighted version of the light level where the light level is divided by the luminous energy. It is a known design issue to implement division in either software or hardware. Nevertheless, in a typical design, there may be limited and discrete luminous energy levels to be provided by the light source control. The division by a known value can be implemented as a multiplication of the inverse of the known value to overcome the issue of implementing a division operation.

Figure 3B:
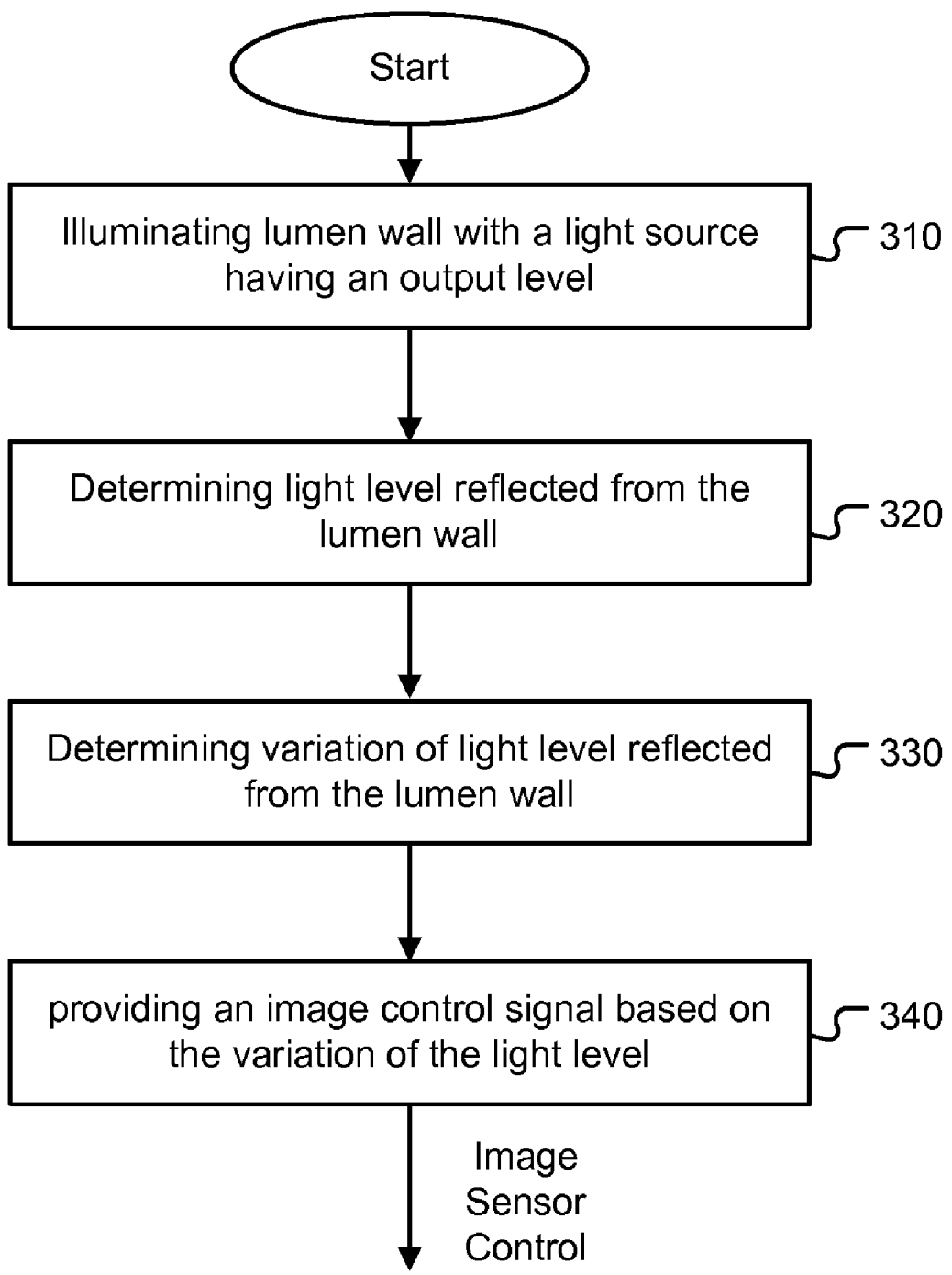
FIG. 3B is a flow chart illustrating exemplary processing to control capsule camera upon detection of capsule camera environment change according to one embodiment of the present system.
Figure 3C:
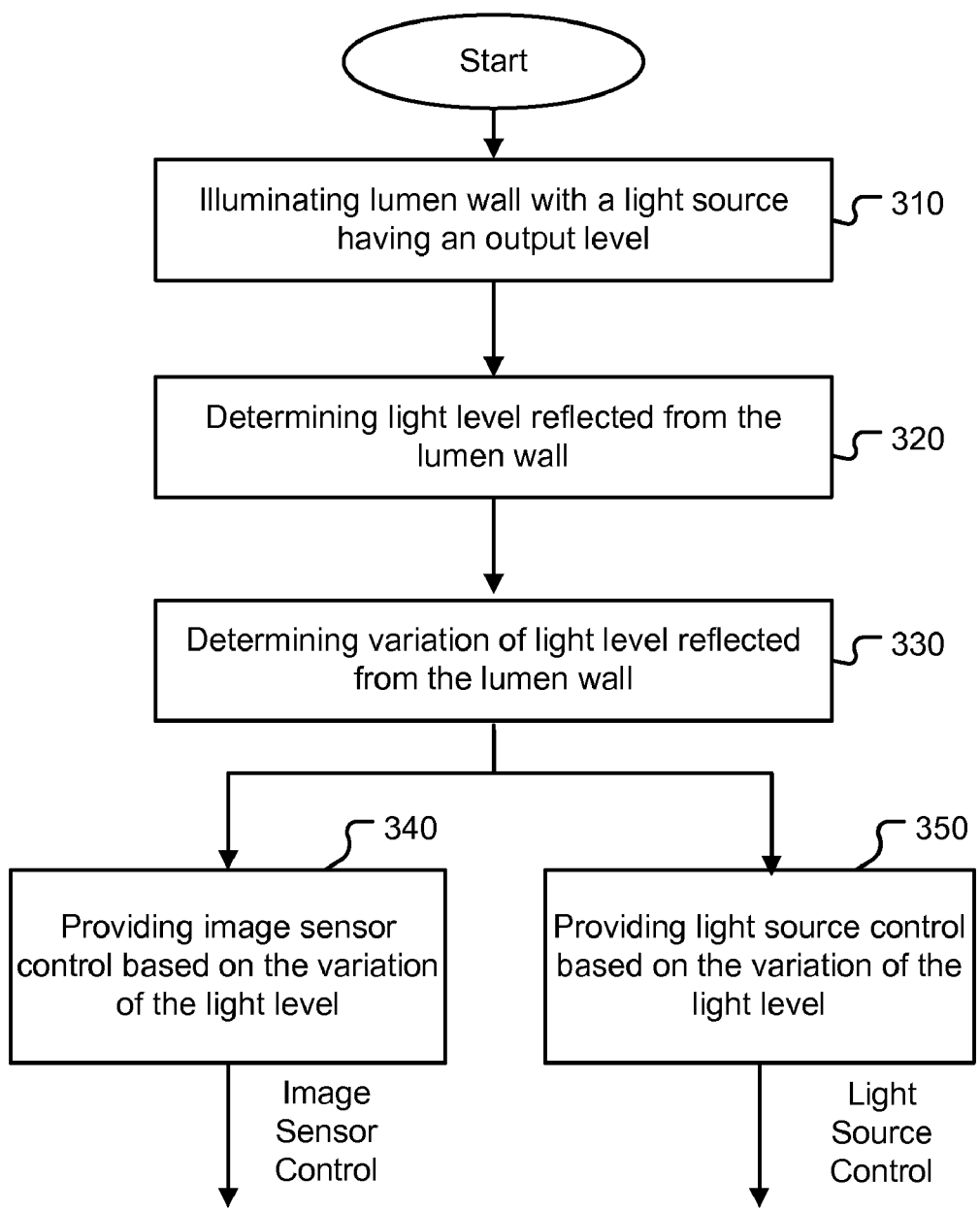
FIG. 3C is a flow chart illustrating exemplary processing to control capsule camera and light source upon detection of capsule camera environment change according to one embodiment of the present system.

FIG. 3B illustrates an exemplary flow chart corresponding to the system of FIG. 2B. The method illustrates an additional step of providing an image control signal based on the variation of the light level 340. As mentioned above, the image control signal may be used to configure the operation parameters for the image sensor 16 such as ROI, spatial sub-sampling ratio, and frame rate. FIG. 3C illustrates an exemplary flow chart corresponding to the system of FIG. 2C. The method illustrates an additional step of providing a light source control signal based on the variation of the light level 350. As mentioned above, the light source control signal may be used to adjust the LED output luminous energy of the illuminating system 12.

When the capsule camera travels in the body cavities, the light level associated with image data sensed by the image sensor 16 may fluctuate due to various reasons, such as the distance and relative angle between the image sensor 16 and the lumen wall 100, and the texture and characteristics of the lumen wall 100. The fluctuation in received light level may falsely trigger the detection of entrance of colon from the small intestine. The fluctuation of light level may be more prominent for image sensor-based light level detection since the image data from the image sensor 16 may correspond to different scenes. The variations of intensity level in the image data may be falsely determined to be a change in received light level. Therefore, certain pre-process may be required to determine light level based on the image data in order to improve the reliability of the entrance of colon detection, the image data has to be properly pre-processed to derive a reliable light level.

Figure 4A:
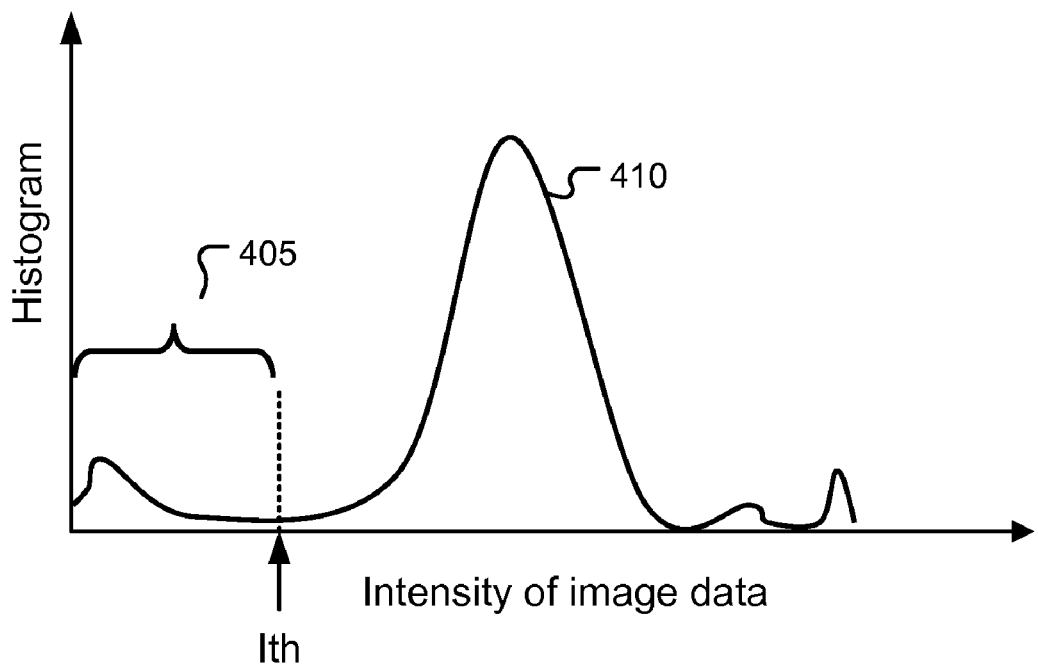
FIG. 4A illustrates a sample histogram of a capsule image without dark areas in the image contents.
Figure 4B:
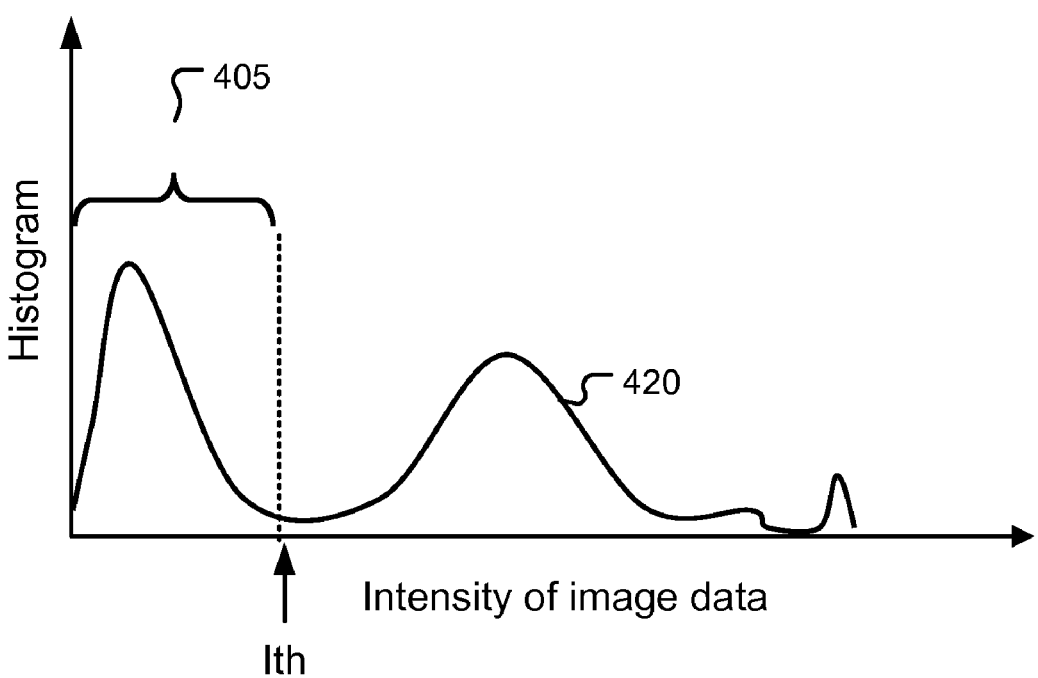
FIG. 4B illustrates a sample histogram of a capsule image having dark areas in the image contents.

FIG. 4A illustrates an example of histogram corresponding to a capsule image that comprises mostly smooth lumen wall without significant dark areas in the scene. The histogram 410 shows that a high concentration of intensity between the lowest and the highest intensity level. FIG. 4B illustrates an example of histogram corresponding to a capsule image that contains significant dark areas in the scene. The histogram 420 shows that high concentration of intensity near the lowest intensity level and another high concentration between the lowest and the highest intensity level. The two images may be subject to similar lighting environment within a same section of the body cavity, such as the small intestine. However, the histogram 420 may be corresponding to an image taken at an area with folded lumen wall. If the received light level is determined according to the overall image, the determined light level may become heavily dominated by the dark areas of FIG. 4B. Therefore, the light level determination has to take into consideration of the dark areas that may appear in the sensed image. In the capsule camera system, there may be some design limitations of the light source that may cause non-uniform illumination within the viewing area of the image sensor. In order to take into account of the variations of illumination within the imaging area, the intensity may be adjusted according to a location-dependent factor to compensate the variation of illumination, which is considered as an additional part of pre-processing applied to an incoming image data. The pre-processing for incoming image data from the image sensor is not discussed in details. Nevertheless, pre-processing of image sensor data is known to an ordinary skilled person in the field. The pre-process may include noise reduction, color pixel demosaicing, color space conversion, and image sharpening.

To overcome the issue of light level dependency on the possible dark areas in the image, a system according to an embodiment of the present invention excludes low intensity levels from light level determination. A low intensity threshold $I_{th}$ is selected where $I_{th}$ is lower than the intensity level anticipated for an un-folded lumen wall. Let I(x,y,n) be the intensity of a pixel at (x,y) location for frame n. The frame intensity I(n) for image frame n is calculated as:

$$I(n) = \sum_{I(x,y,n) > I_{th}} I(x, y, n)/N_n \quad (1)$$

where $N_n$ is the total number of pixels of image frame n that has intensity level greater than $I_{th}$. In other words, the pixels 405 having intensity falling below the threshold $I_{th}$ is excluded from the frame intensity calculation. If pixels of all intensity level are to be counted for the frame intensity of equation (1), the intensity threshold $I_{th}$ can be set to a negative value, such as −1. In this case, the frame intensity of equation (1) becomes the average frame intensity.

The image sensor response to the input light, also called photometric sensitivity, is usually measured as V/lux-sec, where V is the voltage in Volt for the sensor response, lux is the light intensity and sec is the sensor exposure time measured in second. For a capsule camera inside the lumen, the exposure time is essentially the period that the light source is turned on. The product of light intensity and exposure time is the luminous energy collected by the sensor pixel. In typical applications, the light intensity and the exposure time are fixed. When the sensor is operated in the linear range, the pixel output voltage is represented as a linear function of the luminous energy. Therefore, the image intensity level of frame n is a valid measurement of luminous energy of the light source reflected from the lumen wall and collected by the image sensor. In this specification, the measured luminous energy for time instance n is termed as light level L(n) for convenience.

For a point light source, the intensity falls off as the inverse square of the distance from the light source. Therefore, the light intensity l(d) measured at a distance d from the point light source is:

$$l(d) = C1/d^2, \quad (2)$$

where C1 is a constant related to the light power of the point light source. In practice, the light source is not a point light source and the above inverse square relation will have to be modified as $l_1(d) = C1/d^x$ where 0<x<2. The light will be reflected from the lumen wall and collected by the image sensor. Due to the close proximity of the image sensor and the LED inside the capsule camera, the distance between the light source and the lumen wall is substantially the same as the distance between the image sensor and the lumen wall. The reflected light at the image sensor may be modeled as $l_2(d) = C2(n)l_1(d)/d^y = C1 \cdot C2(n)/d^{(x+y)}$, where C2(n) is related to the texture of the scene being imaged and 0<y<2. The coefficient C2(n) will vary from place to place inside the lumen, but the average of C2(n) over large enough samples will converge. Therefore, if the light intensity and exposure time of the light source is fixed, the measured frame intensity according to equation (1) is a good measurement of light level L(n):

$$L(n) \propto I(n) \propto C1 C2(n)/d^{(x+y)} => L(n) = C/d^z, \quad (3)$$

where C=C1·C2 and z=x+y. Based on equation (3), L(n) equals to I(n) multiplied by a constant factor. For simplicity, the measured frame intensity will be used as the light level without the constant factor, i.e., $$L(n) = I(n). \quad (4)$$

As to be discussed later, weighted frame intensity will be used as light level when the luminous energy is not fixed. According to equation (3), the light level is related to the distance between the image sensor and the lumen wall being imaged. The relation depicted in equation (3) may not be an accurate model for practical cases. Nevertheless, the nature that a larger distance will result in a lower light level should be always valid. On the other hand, a smoothed version of C2(n) is expected to converge to a fixed value with enough data samples to average the variation. Therefore the dependency of L(n) on C2(n) may be reduced by smoothing L(n) over a sufficient number of image frames.

In some cases, the light source control may be exercised to adjust the output intensity of the light source, the exposure time of the light source, or a combination of both. In this case, the coefficient C1 becomes a variable C1(n) which will affect the light level measurement. The frame intensity in equation (3) will not only depend on the distance between the image sensor and the lumen wall, but also depend on the particular luminous energy of the light source applied to the particular frame. The dependency on the luminous energy can be removed by modifying the frame intensity I(n) to a weighted frame intensity $I_w(n)$, where the frame intensity is weighted by the luminous energy of the light source applied to image frame n, i.e.:

$$I_w(n) = I(n)/[C_1(n) \cdot \Delta t(n)], \quad (5)$$

where $\Delta t(n)$ is the exposure time at time instance n. In this case, the weighted frame intensity $I_w(n)$ is used as the light level L(n), i.e.:

$$L(n) = I_w(n). \quad (6)$$

When a light sensor is used to determine the light level as shown in FIG. 2D, the light level is readily measured by the light sensor instead of processing the image data to determine intensity level for an image frame as shown in equation (1). While a light sensor usually measures the light intensity for a sustained light source, the light measurement in the capsule camera environment having a flashed light source will be affected by the exposure time of the light source. Therefore, the measured quantity is related to the luminous energy when the light sensor is operated in a linear range. The light intensity and weighted light intensity detected or determined by the light sensor at time n is designated with the same symbol I(n) and $I_w(n)$ respectively as for the case using an image sensor. Hereinafter, the symbol I(n) may refer to the frame intensity of equation (1) or the light intensity measured by a light sensor. Similarly, the symbol $I_w(n)$ may refer to the weighted frame intensity of equation (5) or the weighted light intensity measured by a light sensor. In one embodiment multiple light sensors may be adopted since a single light sensor may not always provide a reliable light measurement. For example, if a light sensor is mounted on the side of the capsule camera and the capsule camera happens to lie on the lumen with light sensor immediately against the lumen. The light sensor will not be able to receive the scattered light. Therefore, multiple light sensors strategically mounted on multiple locations will improve the reliability of the light measurement.

In the above description, a single light source is always referred for discussion. Nevertheless, multiple light sources may be used to provide more uniform or broader illumination coverage. For example, two LED light sources are illustrated in FIGS. 1A and 1B. The multiple light sources can be controlled as a group or individually.

The frame intensity determined may be subject to fluctuation due to the various reasons such as the relative angle between the capsule camera and the lumen wall or the lumen surface situation such as folded or smooth. When a light sensor is used, the light level received is also subject to fluctuation due to various reason such as the relative angle between the light sensor surface and the lumen wall. In addition an area may be illuminated by more than one LED's simultaneously when multiple light sources are used. In order to improve the reliability of the frame intensity or the measured intensity, a moving average of the normalized intensity is used according to:

$$\bar{I}(n) = (1/N1) \sum_{i=0}^{N1-1} I(n-i) \quad (7)$$

where $\bar{I}(n)$ is calculated as a moving average over a window of N1 frame intensity values, $I(n)$, where N1 is an integer that is sufficiently large to smooth out the fluctuation. On the other hand, N1 should be small enough to reflect the dynamics when the capsule camera enters the colon from the small intestine. Consequently, the moving average of the normalized intensity, $\bar{I}(n)$ described in equation (7) is called a short-term average. For example, N1 may be chosen to be 100 for the case that image sensor senses 2 images per second or light sensor measures light level twice per second. Other integer values for N1 may also be used to achieve the same goal of smoothing out the fluctuations. If weighted frame intensity $I_w(n)$ is used, the moving average of the weighted frame intensity $\bar{I}_w(n)$ can be computed similarly according to equation (7).

The moving average method based on a sliding window according to equation (7) implies that storage to hold N1 frame intensity values, $I(n)$, is required. Alternatively, the average $\bar{I}(n)$ can be computed according to an exponential moving average algorithm to remove the requirement of storing N1 frame intensity values $I(n)$:

$$\bar{I}(n) = \alpha I(n) + (1-\alpha)\bar{I}(n-1) \quad (8)$$

where α is parameter for system design and 0<α<1. An α value closer to 1 will cause the moving average $\bar{I}(n)$ to weigh more on a current light level, $I(n)$. Alternatively an α value closer to 0 will cause the moving average $\bar{I}_w(n)$ to weigh less on a current light level $I(n)$. In order to sufficiently smooth out the fluctuation in detected light level, a α value of 0.01 may be selected. Other α values may also be used to achieve the same goal. If the weighted frame intensity is used, the average according to an exponential moving average algorithm can be similarly computed based on equation (8).

While the example described in equation (7) requires N1 values of frame intensity to be used for computing the moving average, alternative methods may achieve the same goal with reduced storage requirement. For example, the storage required for N1 values of frame intensity may be substantial when a large N1 is used. To reduce the storage requirement, every M-th value of the N1 frame intensity values can be stored instead of every value, where M and N1 are selected such that N1 is divisible by M. This reduces the requirement to the 1/M of the original storage.

Upon the determining the moving average of frame intensity value, the variation of the light level can be determined according to:

$$\Delta \bar{I}(n) = \bar{I}_{REF}(n) - \bar{I}(n), \quad (9)$$

where $\bar{I}_{REF}(n)$ is reference value of the moving average of the frame intensity. The $\bar{I}_{REF}(n)$ should represent a long-term average of the frame intensity for the capsule camera when it travels in the small intestine. Therefore, when the capsule camera enters into the colon from the small intestine, there will be noticeable difference between the short-term moving average of frame intensity value and the long-term average of the frame intensity. Furthermore, since the small intestine has a smaller average diameter than the average diameter of the colon, the short-term average light level is expected to become lower when the capsule camera enters the colon. Therefore, a positive value $\Delta \bar{I}_w(n)$ should be observed when the capsule camera enters the colon. In the case that the weighted frame intensity is used, the variation of the weight light level can be similarly determined according to equation (9). In the case that a long-term average of the frame intensity is used as the reference value of the moving average of the frame intensity, the $\bar{I}_{REF}(n)$ can be calculated similarly according to equation (7):

$$\bar{I}_{REF}(n) = (1/N2) \sum_{i=0}^{N2-1} I(n-i) \quad (10)$$

where N2 is substantially larger than N1. For example, N2 can be selected to be 10 times as large as N1. Since N2 is substantially larger than N1, a large number of $I(n)$ values have to be stored. However, if N2 is divisible by N1, i.e., N2/N1=N3, the long-term average can be computed as:

$$\bar{I}_{REF}(n) = (1/N3) \sum_{i=0}^{N3-1} \bar{I}(n-i \cdot N1), \quad (11)$$

Therefore, instead of storing N2 values of $I(n)$, implementation according to equation (10) will only require to store N3 values of $\bar{I}(n)$. Alternatively, the long-term average can be calculated using an exponential moving average method similar to equation (6), $$\bar{I}_{REF}(n) = \alpha' \bar{I}(n) + (1-\alpha')\bar{I}_{REF}(n-1), \quad (12)$$

where α' is substantially smaller than α. For example, α' can be chosen to be 0.1α or smaller. In practice, the environment change sensing mode may be started after some delay upon the administering the capsule camera into the human body. While the capsule camera spends typically 4 to 8 hours before it enters the colon, the capsule camera may start the environment change sensing mode at 2 to 3 hours after the capsule camera is swallowed. This may save the power to operate the capsule camera in the environment change sensing mode during the initial 2 or 3 hours while the system can almost surely to turn on the environment change sensing mode before the capsule camera enters the colon.

While the variation according to equation (8) measures the difference between the long-term moving average of frame intensity and the short-term moving average, other measurement may also be used. For example, a relative variation may be used:

$$\Delta \bar{I}(n)=1-((n)/\bar{I}_{REF}(n)). \qquad (13)$$

Again, the variation $\Delta \bar{I}(n)$ is expected to be a positive value when the capsule camera enters into the colon. If weighted frame intensity is used, the corresponding variations as shown in equations (9) to (13) can be derived similarly.

Upon the determination of the variation of frame intensity, the system compares the variation of frame intensity with a known threshold. If the variation is greater than the threshold, the system determines that an environment change is detected. Otherwise, no environment change is detected. In the environment change sensing mode, the capsule camera system is operated in a very low-power mode where the LED output luminous energy may be reduced and the image sensor may be figured with a small ROI or a large sub-sampling ratio to conserve power. Upon the detection of environment change that may indicate the entrance into the colon from the small intestine, the image control unit 220 may send control signal to the image sensor to change the image sensor configuration for a normal imaging mode and the light control unit 230 may send a control signal to increase the LED output to a normal level. For a skilled person in the art, the same technique could be applied to detect the capsule entering into the small intestine from stomach if the small intestine needs to be imaged. Because the capsule normally stay in stomach for quite some time, for example one hour, before passing the pylorus and enters into the small intestine. Some images could be taken in stomach, for example for the first 2 minutes or first 50 images to establish a moving average. The capsule camera then enters into environment detecting mode to detect the environment change corresponding to entering the small intestine while conserving power. The capsule camera is activated to image the small intestine after detecting environment change corresponding to entering the small intestine.

The processing unit 210, the image control unit 220 and the light control unit for the processing module 17 are shown as separate units in this disclosure for the purpose to describe their respective functions. In practice, they may be implemented by sharing part of the same hardware resources such as digital signal processing module, microcontroller, or Field Programmable Gate Array (FPGA). When these functions are implemented in software, an integrated software codes may be used to support all these functions. Furthermore, the processing module 17 and control module 22 of FIGS. 1A and 1B are shown as separate modules. In practice, the two modules may be integrated into a unified module, or some of functions described for the processing module 17 may be located in the control module 22, or vice versa, some functions for the control module 22 may be located in the processing module 17.

Figure 5:
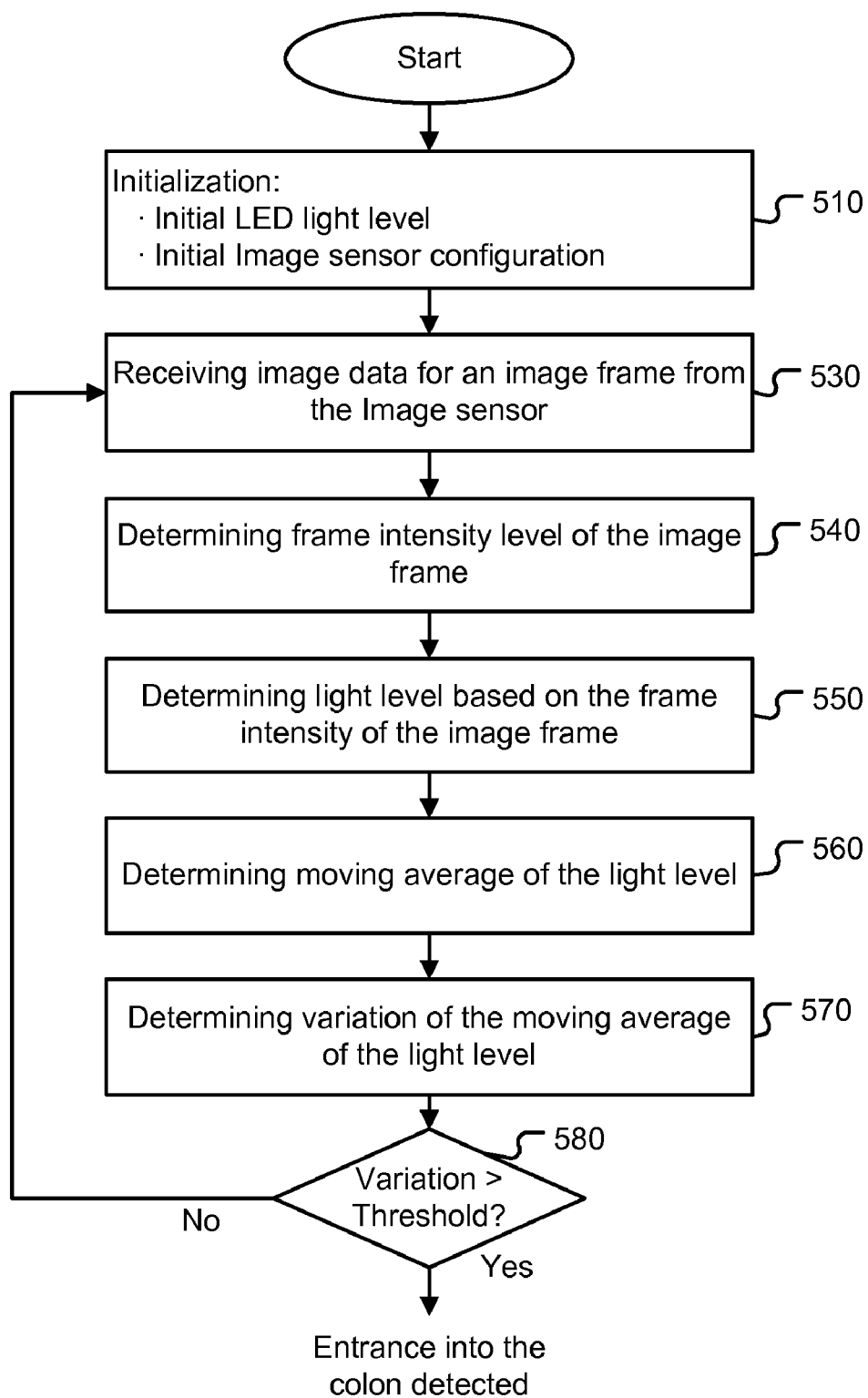
FIG. 5 is a flowchart illustrating an exemplary implementation of a method for detecting the capsule camera environment change based on received light level according to one embodiment.

FIG. 5 illustrates a sample flow chart for the operation associated with the environment change sensing. When the environment change sensing is started, the system performs initialization 510 by initializing LED light output luminous energy and initializing the image sensor configuration. The initialization may include the average sensor image intensity value converge to within a certain range. The system then goes into a loop to detect environment change by starting with receiving image data for an image frame from the image sensor 530. The frame intensity level of the image frame is determined in step 540 and the frame intensity based on the frame intensity of the image frame is determined in step 550. Based on the frame intensity, the moving average thereof is computed in step 560 and the variation of the moving average is computer in step 570. The variation of the moving average is compared again a known threshold at step 580. If the variation is greater than the threshold, an output signal is generated to indicate the environment change. Otherwise, the loop goes back to step 530 to receive the next image data. Depending on the detected environment of the capsule camera, corresponding control signals can be applied to the image sensor and the light source separately. For example, if the capsule camera is intended for imaging the colon, the luminous energy of the light source before entering the colon can be lowered to a level just adequate for the capture control to detect environment change. Similarly, if the image sensor is used to detect the environment change, the image sensor control can be set for output a small image size just adequate for the capture control to detect the environment change. Since the moving average may take some number of images to stabilize, in one embodiment, the initialization process includes a sufficient number of images to stabilize before moving to step 530. Furthermore, as mentioned previously that the capsule camera will take some time after being swallowed before it travels to the small intestine, in one embodiment the starting point of the process of FIG. 5 may begin after a period of delay after the capsule camera is swallowed.

While the light intensity reflected from the lumen wall provides useful information to detect the event when the capsule camera enters the colon from the small intestine, there are various factors that may affect the accuracy of the entrance detection. Besides the variation of reflected light from lumen walls, the average travel speed of the camera may also provide some information to detect the entrance of the capsule camera from the small intestine to the colon. The average small intestine transit time is about 5 hours while the average colon transit time is about 30 hours. On the other hand, the length of the small intestine is about 6 meters and the length of the colon is about 1.5 meters. Therefore, the average transit speed for the small intestine is about 20-30 times faster than that for the colon. Consequently the average transit speed can provide useful information for detecting the entrance of the capsule camera into the colon from the small intestine. Nevertheless, it may be difficult to compute the average transit speed efficiently and accurately because it would require to measure the distance that the capsule camera travels over a period of time.

To overcome the issue of speed measurement, an embodiment according to the present invention is disclosed that computes a metric correlated with the average transit speed. In the US patent application, entitled "In Vivo Autonomous Camera with On-Board Data Storage or Digital Wireless Transmission in Regulatory Approved Band", Ser. No. 11/533,304, filed on Sep. 19, 2006, a method for operating a capsule camera is disclosed, wherein the method comprises detecting a motion based on a difference between two captured images and evaluating the motion to determine whether to store the current image based on a metric on the motion. The motion metric described in the above patent application can be used to derive an indication of entrance of capsule camera into the colon from the small intestine or used with other environment sensing technique as additional information to assist the detection of entrance of the capsule camera into the colon from the small intestine. In the capsule camera system, the time interval that the capsule camera traveled can be measured in various ways. For example, the camera sensor may be operated with a fixed frame rate and the count of the frames can be used as a measure of corresponding time interval. Heuristically, when motion metric is measured for two images corresponding to an image captured at a first location and a second location where the second location corresponds to new location after the camera moves, a larger distance traveled will result in larger differences between the two images. The larger differences between the two images will cause the motion metric to exceed a threshold more likely. Consequently, the number of frames which have a motion metric exceeding a threshold is correlated with the distance that the capsule camera traveled over a period of time. Since the system disclosed in the U.S. patent application Ser. No. 11/533,304 has the capability of computing the motion metric, the use of motion information to detect the entrance or to assist the entrance detection would only incur a very small system cost. Nevertheless, any capsule camera system may incorporate the embodiment of the present invention to detect environment change or to use with other technique for enhancing the reliability and accuracy of entrance detection of the capsule camera into the colon from the small intestine.

In the U.S. patent application Ser. No. 11/533,304, a method for operating a capsule camera is disclosed which includes detecting a motion based on a difference between a current digital image and a reference digital image, and evaluating the motion to determine whether to delete the current digital image or to store it in the archival memory based on a metric on the motion. When the motion metric exceeds a threshold, the current digital image is stored in the archival memory and the current digital image becomes the reference digital image for processing the next incoming digital image. When the motion metric is below the threshold, the current digital image is deleted and the reference digital image remains intact for processing the next incoming digital image. For the purpose of entrance detection of the capsule camera into the colon from the small intestine, the decision regarding whether there is movement between two digital images may use a threshold different from that for the decision regarding whether to store or delete the current image. Furthermore, the digital image may not need to be stored when a movement detected if there is no interest or no intent of examining the small intestine.

The motion metric measured can provide useful information for assessing the environment. As mentioned earlier, the capsule camera travels faster in the small intestine than in the colon. It is anticipated to observe larger motion metric in the small intestine than in the colon. In other words, the environment change can be detected based on the characteristics of the motion metric. The following example illustrates the use of motion metric to estimate the moving speed of the capsule camera in the lumen. Let D(m) be the motion decision made for image frame m. The motion decision is made for frame m based on the motion metric, i.e.

$$D(m) = \begin{cases} 1, & \text{if motion metric} \geq \text{motion threshold, and} \\ 0, & \text{if motion metric} < \text{motion threshold} \end{cases} \quad (14)$$

The frame index m may be different from the frame index n used for the frame intensity computation as shown in equation (1). For example, the sensor may be operated at a frame rate of 2 frames per second and the image intensity is measured at the same rate as the operating rate of the sensor. On the other hand, every fourth frame of the sensor output may be used, an example, for motion metric evaluation as to determine whether the motion metric is exceeding the threshold. In this example, the index m corresponds to a frame rate of 0.5 frame per second. In another example, the index m may correspond to a frame rate higher than the frame rate for index n. In yet another example, the index m may correspond to a frame rate the same as the frame rate for index n.

The capsule camera typically travels a few hours in the small intestine before it enters the colon. The average travel speed of the capsule camera travelling in the small intestine can be estimated over a relatively long time period to smooth out fluctuations during the course of transit in the small intestine. On the other hand, a short-term average speed should be monitored to quickly detect a change from the long term average speed, wherein the change in the short-term average speed from the long-term average speed may indicate the entrance from the small intestine to the colon. The time period for the short-term average speed estimate should be short enough to reflect the dynamic nature of speed changes when the capsule camera enters the colon from the small intestine.

The short-term average speed, $S_S(m)$ of the capsule camera travelling through the organs can be estimated according to:

$$S_S(m) = \frac{C3}{T_S} \sum_{i=0}^{N_S-1} D(n-i) \quad (15)$$

where $T_S$ is the time interval for short-term average speed, $N_S$ is the number of frames being assessed for motion metric within the time interval $T_S$, and C3 is a constant. The short-term average speed can be calculated every time that a decision D(m) is made and it may involve quite some computations for each frame. Alternatively, the computation can be simplified to be performed once every $N_S$ frames, where the short-term average speed is only estimated for $S_S(m+i \cdot N_S)$, where i=0, 1, 2, . . . . In this case, the average transit speed will be used for the entrance decision at time instances $T_S$ apart. The short-term average speed can be compared with a reference average speed to detect any noticeable change as an indication of entrance into the colon from the small intestine. The long-term average speed can be used as the reference average speed, $S_{REF}$ to be compared with the short-term average speed, where the long-term average speed can be calculated as:

$$S_L(m) = \frac{C3}{T_L} \sum_{i=0}^{N_L-1} D(m-i) \quad (16)$$

where $T_L$ is the time interval for long-term average speed and $N_L$ is the number of frames being assessed for motion metric within the time interval $T_L$. The long-term interval should be much longer than the short-term interval, such as 10 times or more. When the long-term average speed is selected to be a multiple of the short-term interval, i.e., $N_L = N4 \cdot N_S$, the long-term average speed can be calculated from the short-term average speed:

$$S_L(m) = \sum_{i=0}^{N4-1} S_S(m - i \cdot N_S) \quad (17)$$

While the above long-term average speed can be used as the reference average speed to be compared with the short-term average speed to determine if there is an indication of entrance into the colon from the small intestine, other suitable measure may be used also as the reference average speed. For example, a previous short-term average speed such as $S_S(m-N5 \cdot N_S)$ where N5 is an integer or a filtered short-term average speed, $\overline{S}_S(m)$ such as:

$$\overline{S}_S(m) = \sum_{i=-N6}^{N6} C4(i) \cdot S_S(m - N5 \cdot N_S - i \cdot N_S) \quad (18)$$

where C4(i) is filter coefficients and N6 is the window size that the short-term average speed to be filtered on each side of $S_S(m-N5 \cdot N_S)$.

The short-term and long-term average speeds specified in equations (15) through (17) imply that some memory space is required to store the D(m) and $S_S(m)$ values and a number of addition operations are required. Alternatively, these values can be computed iteratively to save storage space and computation. For example, the short-term average speed can be calculated according to an exponential moving average as:

$$S_S(m) = \alpha 1 \cdot D(m) + (1 - \alpha 1) S_S(m-1). \quad (19)$$

Similarly, the long-term average speed can be computed as:

$$S_L(m) = \alpha 2 \cdot D(m) + (1 - \alpha 2) S_L(m-1). \quad (20)$$

The weighting factors $\alpha 1$ and $\alpha 2$ are used to control the weight of the current decision D(m) for the average speed calculation. A smaller $\alpha 1$ or $\alpha 2$ value will cause a longer term average. For example, $\alpha 1$ may be set to 0.01 and $\alpha 2$ may be set to 0.001 to obtain a proper weight for the short-term and long-term average speeds. In general, the factor $\alpha 1$ should be 10 times larger than the factor $\alpha 2$ or more so that the long-term average speed will have the effect of be contributed by more data samples than the short-term average speed. The above $\alpha 1$ and $\alpha 2$ values are for illustration purpose and are not posing any limit to the present invention.

When the short-term average speed is estimated, it is compared with a reference average speed to assess the variation. If the variation exceeds a threshold, an indication of entrance into the colon from the small intestine is asserted. The variation of short-term average speed can be evaluated as:

$$\Delta S_S(m) = S_{REF}(m) - S_S(m). \quad (21)$$

where the reference average speed $S_{REF}(m)$ may be the long-term average speed as shown in equation (15), (16) or (19), or a previous short-term average speed, $S_S(m-N_2 \cdot N_S)$ or a filtered short-term average speed as shown in equation (17). The short-term average speed variation can be alternatively defined to be associated with the ratio of the short-term average speed and the reference short-term average speed:

$$\Delta S'_S(m) = 1 - S_S(m)/S_{REF}(m). \quad (22)$$

The variation as shown in equation (21) or (22) based on the estimated short-term average speed can be compared against a threshold to determine whether a detection of entrance into the colon from the small intestine is asserted. For the variation based on equation (21), a transition from the small intestine into the colon is expected to result in a decrease in $S_S(m)$ while $S_{REF}(m)$ remains relatively un-changed. Therefore, it is expected to that the $\Delta S_S(m)$ value will increase when the capsule camera enters the colon from the small intestine. Similarly, it is expected that the $\Delta S'_S(m)$ value will increase when the capsule camera enters the colon from the small intestine. Accordingly, the variation of the short-term average speed can be used to indicate the entrance of capsule camera into the colon from the small intestine.

Figure 6:
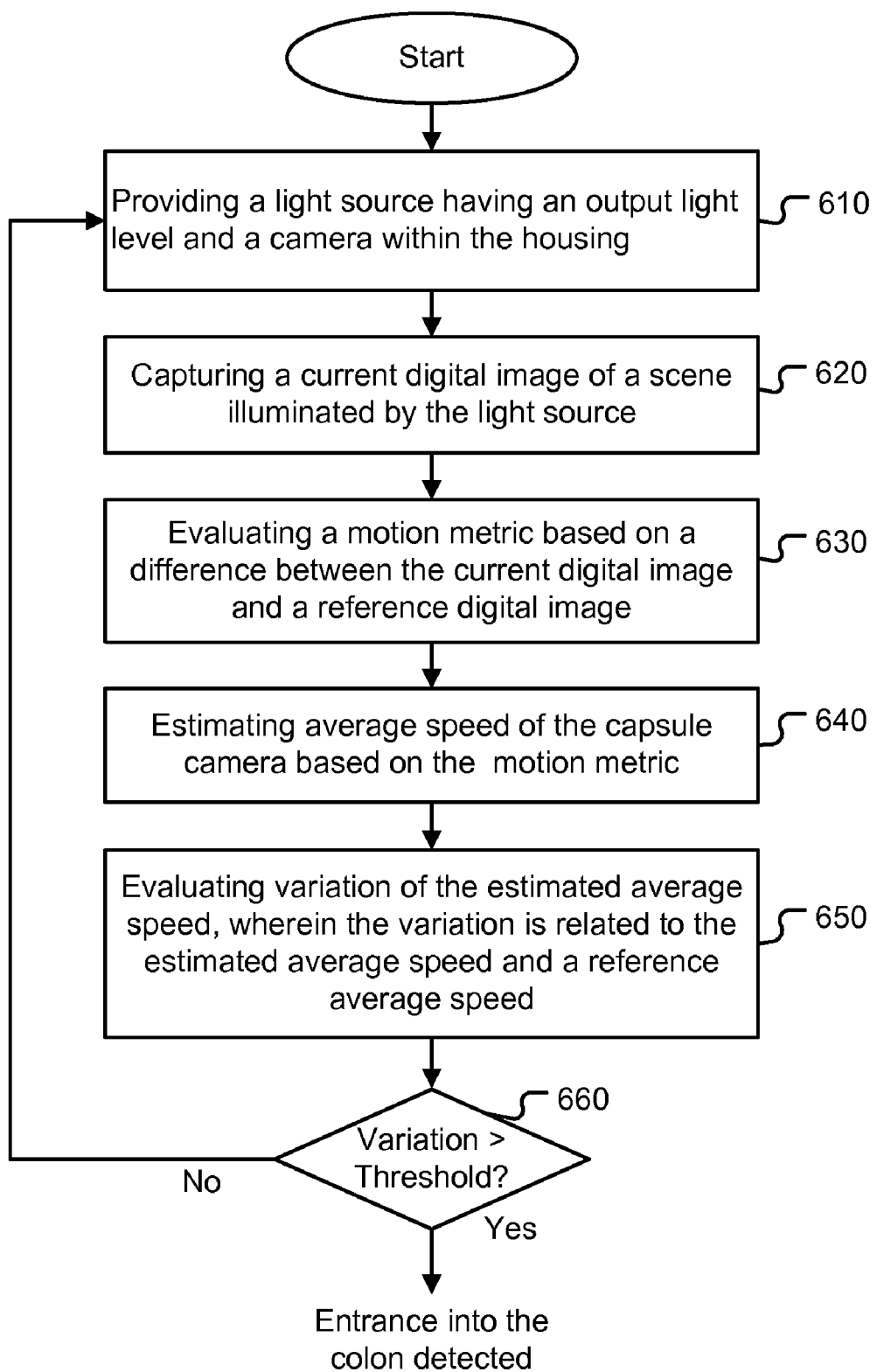
FIG. 6 is a flowchart illustrating an exemplary implementation of a method for detecting the capsule camera environment change based on motion metric between a current frame and a reference frame according to another embodiment.

FIG. 6 illustrates an exemplary flowchart of one embodiment according to the present invention. To use the motion detection based technique for environment change detection, the method begins with providing a light source having a luminous energy 610. The image sensor is then used to capture a current digital image of a scene illuminated by the light source as shown in step 620. A motion metric based on a difference between the current digital image and a reference digital image is then evaluated in step 630 and the motion metric is used for average speed estimation in step 640. The average speed can be estimated based on the motion metric by counting the number of frames that have associated motion metric exceeding a threshold as described earlier in this specification. Furthermore, an exponential moving average can also be applied to compute the average speed based on the motion decision of frames. When the average speed is estimated, the variation of the estimated average speed is calculated as shown in step 640. The variation is used to determine whether the entrance into the colon is detected in step 660. If the variation exceeds the threshold, an indication of the entrance into the colon is asserted. The capsule camera may be operated accordingly for the colon environment. For example, if the capsule camera is intended for imaging the colon, the image sensor control and the light source control can be set properly to capture and store images at desired resolution/picture size and image intensity. If the variation is below the threshold, an indication of the entrance into the colon is not asserted and the capsule camera deems to be still in the small intestine. Accordingly, the capsule camera will remain in a very low-power environment change sensing mode.

The variation of frame intensity as disclosed earlier can be used jointly with the variation of estimated average short-term speed to determine the entrance of capsule camera into the colon from the small intestine. The measurement of luminous energy and the measurement of motion are two independent measurements. When the capsule camera enters into the colon from the small intestine, the diameter of the cavity will become larger and the average travel speed will become slower. An entrance detection based on both factors jointly will surely enhance the reliability of the entrance detection. The variations of the moving average of the light level and the estimated average speed can be compared with their respective threshold individually. If indications based on the moving average of the light level and the estimated average speed are both asserted, the entrance of the capsule camera into the colon can be asserted. Other criterion for the entrance detection may also be used. For example, a single joint variation can be formed as a sum of the variation of the moving average of the light level and the variation of the estimated average speed. The single joint variation is then compared against a threshold to determine whether an entrance into the colon is detected. A higher weighting factor can be used for the variation that is considered to be more important for the associated measurement. For example, if the luminous energy measurement is considered to be more important for the entrance detection, a higher weighting factor can be used for the variation of the moving average of the light level. As yet another example, the threshold for the variation of the moving average of the light level and the threshold for the variation of the estimated average speed are adaptively adjusted. For example, if one variation is substantially larger than its corresponding threshold, i.e. it is a strong indication of entrance detection, the threshold for the other variation may be lowered. In this case, the other variation will be used as a secondary factor to support the decision based on the first variation.

Figure 7:
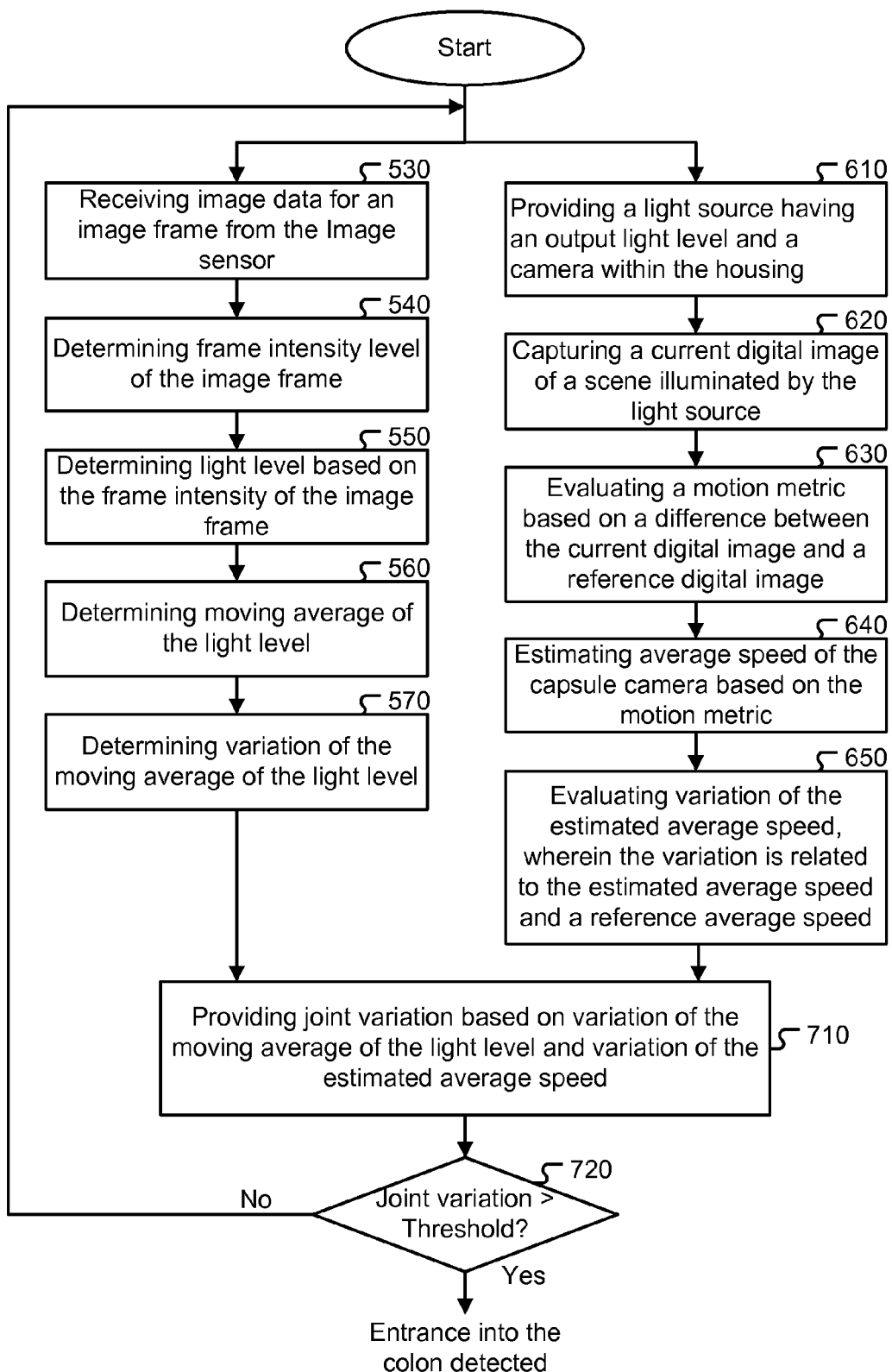
FIG. 7 is a flowchart illustrating an exemplary implementation of a method for detecting the capsule camera environment change based on received light level and motion metric between a current frame and a reference frame according to yet another embodiment.

FIG. 7 illustrates an exemplary flowchart according to another embodiment of the present invention, wherein the environment change detection is based on both the motion metric and the received light energy. As shown in FIG. 7, the flowchart consists of two main branches: one corresponds to the light energy based approach and the other corresponds to the motion metric based approach. The steps 530 through 570 are associated with the evaluation of the variation of the moving average of the light level. The steps 610 through 650 are associated with the evaluation of the variation of the estimated average speed. The variation of the moving average of the light level and the variation of the estimated average speed form a joint variations in step 710 and the joint variation is compared a threshold to determine if an environment change is detected in step 720.

The above detailed description illustrates the specific embodiments of the present invention and is not intended to be limiting. Numerous modifications and variations within the scope of the invention are possible. The present invention is set forth in the following claims.

The invention claimed is:

1. A method for operating a capsule camera having an image sensor, the method comprising:
    illuminating lumen wall with at least one light source having light source control;
    determining light level scattered from the lumen wall;
    determining variation of the light level;
    determining environment of the capsule camera based on the variation of the light level;
    wherein the environment of the capsule camera comprises inside of small intestine, inside of stomach and inside of colon; and
    wherein the variation of the light level is calculated based on the determined light level weighted by luminous energy of said at least one light source.

2. The method of claim 1, further comprising providing image sensor control to the image sensor based on the environment of the capsule camera.

3. The method of claim 1, further comprising providing the light source control to said at least one light source based on the environment of the capsule camera.

4. The method of claim 1, wherein the light level is determined using at least one light sensor.

5. The method of claim 1, wherein the light level is determined using the image sensor of the capsule camera to provide image data of an image frame.

6. The method of claim 5 further comprising processing the image data to determine frame intensity by excluding low intensity levels of the image frame.

7. The method of claim 1, wherein the variation of the light level is related to a plurality of the light levels corresponding to a present instance and at least one past instance.

8. The method of claim 7, wherein the variation of the light is related to a moving average of the plurality of the light levels.

9. The method of claim 8, wherein the variation of the light level is related to a difference between the moving average and an initial average light level.

10. The method of claim 8, wherein the variation of the weighted light level is related to a ratio of the moving average and an initial average light level.

11. A capsule camera system having an image sensor to capture in vivo images inside a lumen, comprising:
    at least one light source having light source control within to illuminate lumen wall;
    a light detecting device to determine light level scattered from the lumen wall;
    a processing unit to determine variation of the light level, and wherein the processing unit determines environment of the capsule camera based on the variation of the light level;
    wherein the environment of the capsule camera comprises inside of small intestine, inside stomach and inside of colon; and
    wherein the variation of the light level is calculated based on the determined light level weighted by luminous energy of said at least one light source.

12. The system of claim 11, further comprising an image control unit to provide an image sensor control signal to the image sensor based on the environment of the capsule camera.

13. The system of claim 12, wherein the processing unit and the image control unit are integrated into a single unit.

14. The system of claim 11, further comprising a light control unit to provide the light source control to said at least one light source based on the environment of the capsule camera.

15. The system of claim 14, wherein the processing unit and the light control unit are integrated into a single unit.

16. The system of claim 11, wherein at least one light sensor is used as the light detecting device.

17. The system of claim 11, wherein the image sensor of the capsule camera system is used as the light detecting device.

18. A method for operating a capsule camera having an image sensor, the method comprising:
    providing at least one light source having light source control to illuminate lumen wall;
    determining light level scattered from the lumen wall;
    determining variation of the light level;
    capturing a current digital image of a scene illuminated by said at least one light source;
    evaluating a motion metric based on the current digital image and a reference digital image;
    determining characteristic of the motion metric;
    determining environment of the capsule camera based on a combination of the variation of the light level and the characteristic of the motion metric;
    providing at least one control selected from a group comprising the light source control to said at least one light source and image sensor control to the image sensor based on the environment of the capsule camera;
    wherein the environment of the capsule camera comprises inside of small intestine, inside of stomach and inside of colon; and
    wherein the variation of the light level calculated based on the determined light level weighted by luminous energy of said at least one light source.

19. A capsule camera system to capture in vivo images inside a lumen, comprising:
    at least one light source having light source control to illuminate lumen wall;
    a light detecting device to determine light level scattered from the lumen wall;
    a first processing unit to determine variation of the light level;
    an image sensor to capture a current digital image of a scene illuminated by said at least one light source;

a second processing unit to evaluate a motion metric based on the current digital image and a reference digital image, wherein the second processing unit further determines characteristic of the motion metric;

a third processing unit to determine environment of the capsule camera based on a combination of the variation of the light level and the characteristic of the motion metric;

a control unit to provide at least one control selected from a group comprising the light source control to said at least one light source and image sensor control signal to the image sensor based on the environment of the capsule camera;

wherein the environment of the capsule camera comprises inside of small intestine, inside stomach and inside of colon; and wherein the variation of the light level is calculated based on the determined light level weighted by luminous energy of said at least one light source.

* * * * *